US010413711B2

(12) United States Patent
Lüttge et al.

(10) Patent No.: US 10,413,711 B2
(45) Date of Patent: Sep. 17, 2019

(54) INTEGRATED MICRONEEDLE ARRAY AND A METHOD FOR MANUFACTURING THEREOF

(71) Applicant: MyLife Technologies B.V., Leiden (NL)

(72) Inventors: Regina Lüttge, Enschede (NL); Svetlana Nikolajevna Bystrova, Hengelo (NL); Joost Gerardus van Bennekom, Enschede (NL); Maciej Domanski, Hengelo (NL); Patrick Wilhelmus Hendrikus Loeters, Deventer (NL); Rob Gerhardus Hendrikus Lammertink, Hengelo (NL); Aloysius Johannes Antonius Winnubst, Enschede (NL)

(73) Assignee: MyLife Technologies B.V., Leiden (NL)

( * ) Notice: Subject to any disclaimer, the term of this patent is extended or adjusted under 35 U.S.C. 154(b) by 1123 days.

(21) Appl. No.: 14/075,954

(22) Filed: Nov. 8, 2013

(65) Prior Publication Data

US 2014/0066855 A1 Mar. 6, 2014

Related U.S. Application Data

(62) Division of application No. 12/922,450, filed as application No. PCT/NL2009/050118 on Mar. 11, 2009, now Pat. No. 8,603,384.

(30) Foreign Application Priority Data

Mar. 11, 2008 (EP) .................................... 08152571

(51) Int. Cl.
*A61M 37/00* (2006.01)
*B81C 99/00* (2010.01)

(52) U.S. Cl.
CPC ..... *A61M 37/0015* (2013.01); *B81C 99/0085* (2013.01); *A61M 2037/0023* (2013.01);
(Continued)

(58) Field of Classification Search
CPC ...... A61M 37/0015; A61M 2037/0023; A61M 2037/003; A61M 2037/0053; A61M 2037/0046
See application file for complete search history.

(56) References Cited

U.S. PATENT DOCUMENTS 3,964,482 A 6/1976 Gerstel et al.
4,557,723 A 12/1985 Sibalis
(Continued)

FOREIGN PATENT DOCUMENTS

JP 7-178326 A 7/1995
JP 2003-033336 A 2/2003
(Continued)

OTHER PUBLICATIONS

Park et al. "Biodegradable polymer microneedles: Fabrication, mechanics and transdermal drug delivery," Journal of Controlled Release, Feb. 2, 2005, 51-66 pp.
(Continued)

*Primary Examiner* — Nathan R Price
*Assistant Examiner* — Courtney B Fredrickson
(74) *Attorney, Agent, or Firm* — Patent Law Works LLP

(57) ABSTRACT

The invention relates to a method of manufacturing of a microneedle array comprising the steps of selecting a soft production mold comprising a set of microscopic incisions defining geometry of the microneedles, said soft production mold being capable of providing the microneedle array integrated into a base plate; using a filler material for abundantly filling the microscopic incisions of the soft production mold thereby producing the microneedle array (Continued)

with pre-defined geometry integrated into the base plate; wherein for the filler material a water or alcohol based ceramic or polymer-ceramic slurry is selected. The invention further relates to a microneedle array 16, a composition comprising a microneedle array, a system for enabling transport of a substance through a barrier and a system for measuring an electric signal using an electrode.

8 Claims, 7 Drawing Sheets

(52) U.S. Cl.
CPC ............... *A61M 2037/0046* (2013.01); *A61M 2037/0053* (2013.01); *B81B 2201/055* (2013.01); *B81B 2203/0361* (2013.01); *B81C 2201/034* (2013.01)

(56) References Cited

U.S. PATENT DOCUMENTS

| | | | |
|---|---|---|---|
| 4,622,031 A | 11/1986 | Sibalis | |
| 4,640,689 A | 2/1987 | Sibalis | |
| 4,802,493 A | 2/1989 | Maganias | |
| 5,135,479 A | 8/1992 | Sibalis et al. | |
| 5,224,925 A | 7/1993 | Varn | |
| 5,238,569 A | 8/1993 | Soria et al. | |
| 5,591,123 A | 1/1997 | Sibalis et al. | |
| 5,605,536 A | 2/1997 | Sibalis | |
| 5,676,850 A | 10/1997 | Reed et al. | |
| 5,746,711 A | 5/1998 | Sibalis et al. | |
| 5,865,786 A | 2/1999 | Sibalis et al. | |
| 6,132,755 A | 10/2000 | Eicher et al. | |
| 6,454,755 B1* | 9/2002 | Godshall | A61M 37/0015 424/449 |
| 2002/0082543 A1* | 6/2002 | Park | A61B 5/1411 604/21 |
| 2002/0138049 A1* | 9/2002 | Allen | A61B 5/14514 604/272 |
| 2004/0220535 A1* | 11/2004 | Canham | C12M 35/00 604/272 |
| 2005/0251088 A1* | 11/2005 | Kwon | A61K 9/0021 604/60 |
| 2006/0172541 A1* | 8/2006 | Lee | A61M 37/0015 438/702 |
| 2009/0099427 A1* | 4/2009 | Jina | A61B 5/14532 600/309 |

FOREIGN PATENT DOCUMENTS

| | | |
|---|---|---|
| JP | 2007-89792 A | 4/2007 |
| WO | 2004/024224 A1 | 3/2004 |
| WO | 2008/020632 A1 | 8/2007 |
| WO | WO 2008016331 A1 * | 2/2008 ........ A61M 37/0015 |

OTHER PUBLICATIONS

Luttge, Regina et al., Integrated lithographic molding for microneedle-based devices, Journal of Microelectromechanical Systems, IEEE Service Center, Aug. 1, 2007, vol. 16, Issue 4, pp. 872-884, Piscataway, NJ, USA.

Ma, Jingtao et al., Gelcasting of alumina ceramics in the mixed acrylamide and polyacrylamide systems, Journal of the European Ceramic Society, Elsevier Science Publishers, Dec. 1, 2003, vol. 23, Issue 13, pp. 2273-2279, Great Britain.

PCT International Search Report and Written Opinion, International Application No. PCT/NL2009/050118, dated Jun. 3, 2009, 11 pages.

Zang, Dou, et al., "Microfabrication of Three-Dimensional, Free-Standing Ceramic MEMS Components by Soft Moulding", Advance Engineering Materials, Dec. 2003; Wiley-VCH Verlag GMBH & Co., vol. 5, No. 12, pp. 924-927, Germany.

* cited by examiner

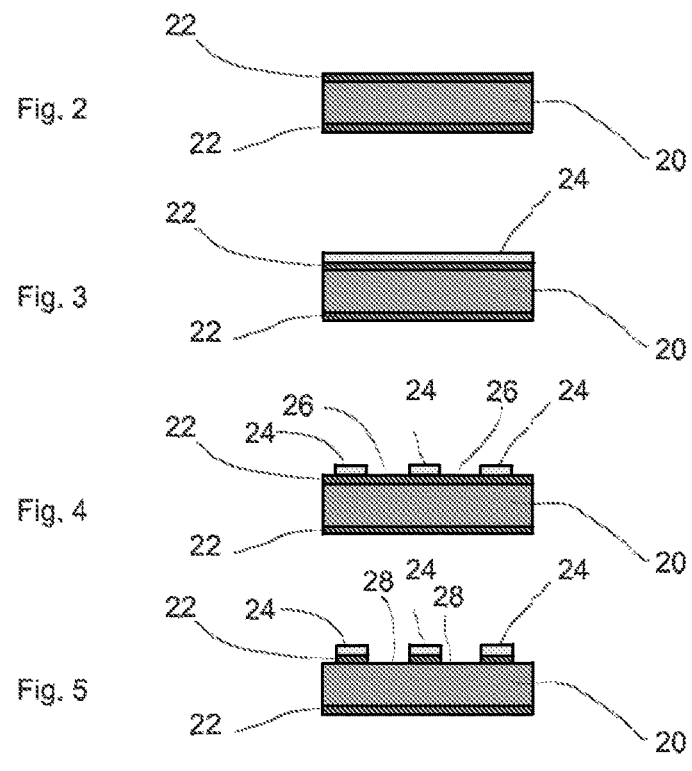
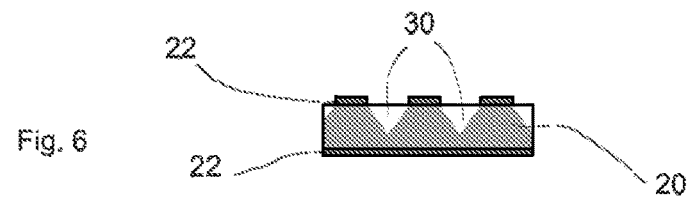
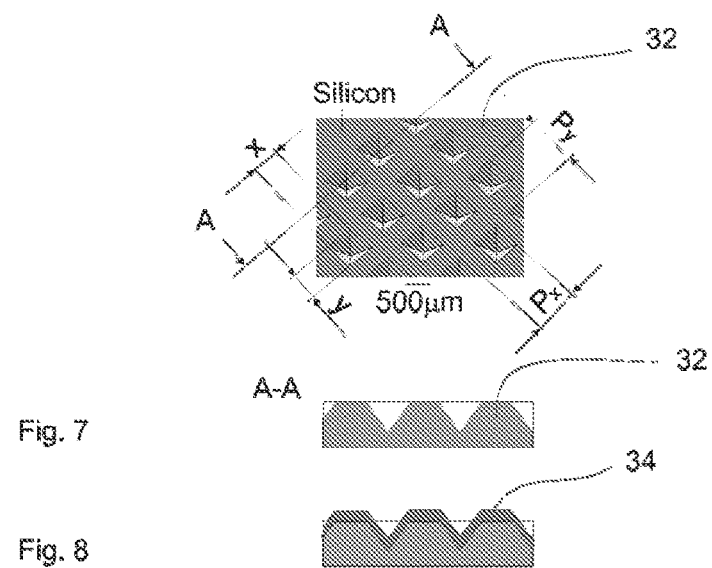

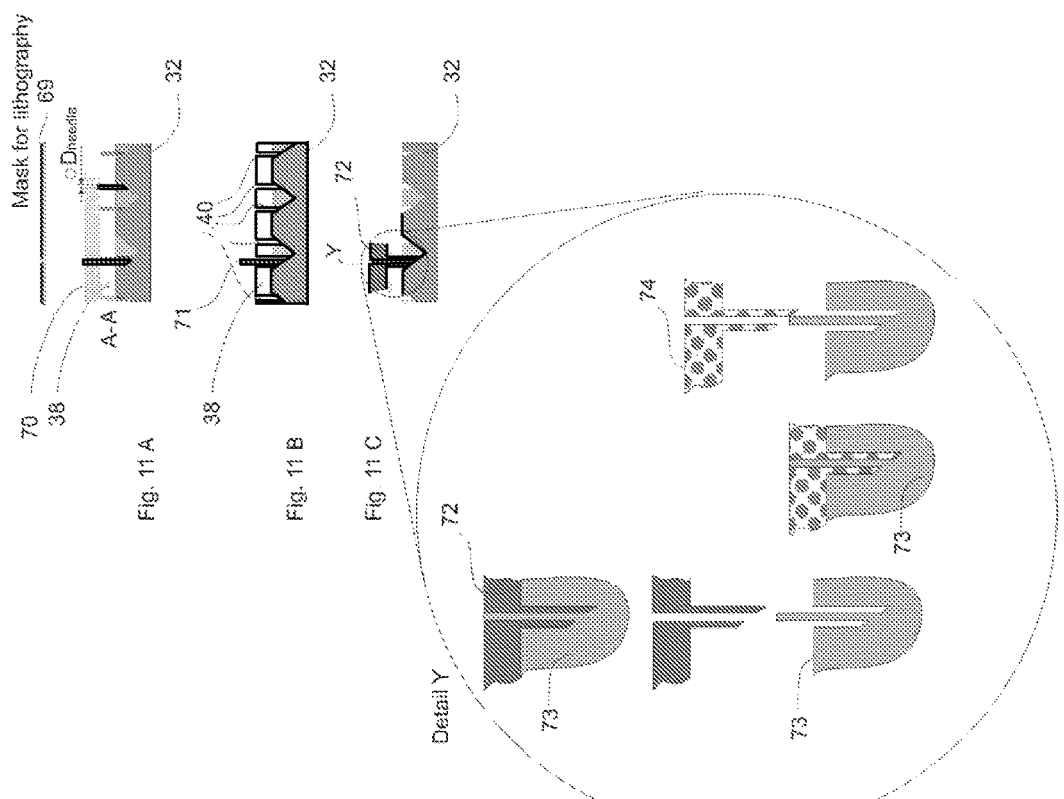

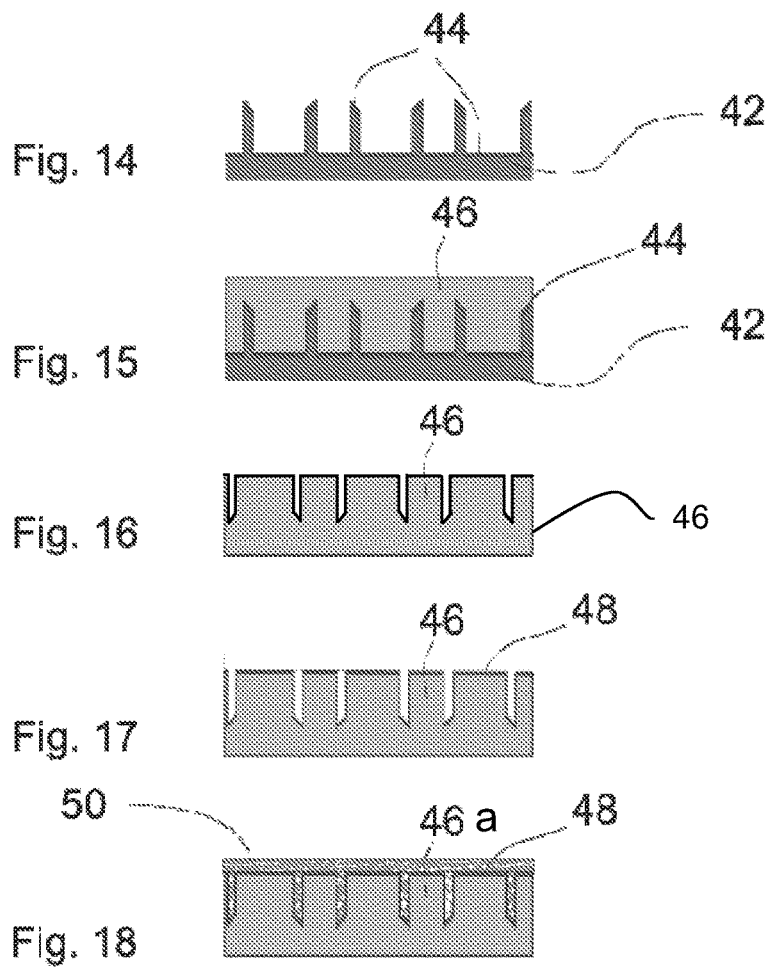
Fig. 14
Fig. 15
Fig. 16
Fig. 17
Fig. 18
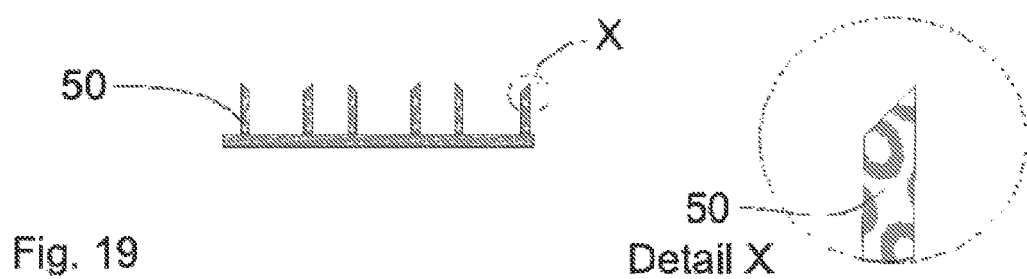
Fig. 19
Detail X

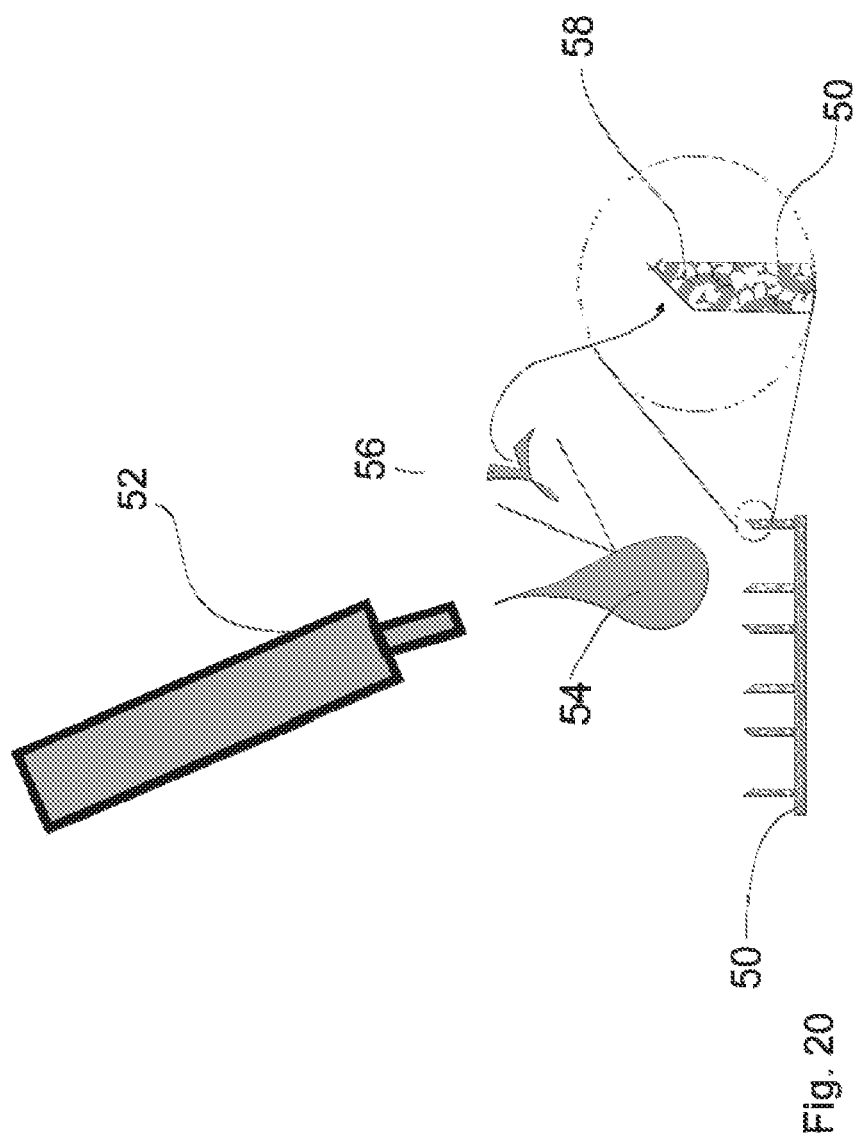

INTEGRATED MICRONEEDLE ARRAY AND A METHOD FOR MANUFACTURING THEREOF

CROSS-REFERENCE TO RELATED APPLICATION

This application is a divisional of U.S. application Ser. No. 12/922,450, filed on Dec. 6, 2010 as the U.S. National Phase under 35 U.S.C. § 371 of International Application PCT/NL2009/050118, filed Mar. 11, 2009, which claims priority to European Patent Application No. 08152571.9, filed Mar. 11, 2008, which are hereby incorporated by reference in their entirety.

FIELD OF THE INVENTION

The invention relates to a method of manufacturing a microneedle array. The invention further relates to a microneedle array and a composition comprising the microneedle array. The invention still further relates to a system for transporting substances across a material barrier. The invention still further relates to a system for measuring of an electrical signal using an electrode.

BACKGROUND OF THE INVENTION

An embodiment of the microneedle array is known from WO 02/064193. The known microneedle array comprises a set of microneedles of a suitable geometry projecting as an out of plane structure from a base support. The known microneedle array may be produced using conventional methods used to make integrated circuits, electronic packages and other microelectronic devices, which may be augmented by additional methods used in the field of micromachining and micromolding. The known three-dimensional arrays of microneedles can be fabricated using combinations of dry-etching processes; micromold creation in lithographically-defined polymers and selective sidewall electroplating, or direct micromolding techniques using epoxy mold transfers. The known microneedle array is formed from a suitable polymer material and can be produced using (i) etching the polymer microneedle directly, (ii) etching a mold and then filling the mold to form the polymer microneedle product, or (iii) etching a microneedle master, using the master to make a mold and then filling the mold to form the polymer microneedle replica of the master.

Over the recent years more and more microneedles have become popular to penetrate the skin barrier and thus introduce means for creating a microfluidic pathway across the skin either for drug delivery, or for analytics of extracted fluids. Microneedles as known in the art may be used in skin patches, in particular in skin patches for delivering a drug across a barrier, for example, skin. So-called intelligent patches, comprising means for delivery of a drug having relatively big molecules, are described in J.-H. Park et al "Polymer particle-based micromolding to fabricate novel microstructures", Biomed Microdevices (2007) 9: 223-234. However, commercialization of such intelligent skin patches having porosity as an actual functional feature has been difficult due to lack of inexpensive production method as well as due to lack of suitable production materials for patch production with required properties.

The known microneedle production method according to WO 02/064193 has a disadvantage that the method of producing microneedle arrays is relatively expensive. The method of microneedle production according to J.-H. Park et al has a disadvantage that the resulting porous microneedles are relatively fragile.

SUMMARY OF THE INVENTION

It is an object of the invention to provide an inexpensive and robust microneedle array having improved properties, wherein parameters of the microneedle array can be optimized easily on demand. For example, such parameters may relate to a tip shape or arrangements of a variety of tip shapes within one array, diameter of the microneedles, their length, as well as their density in the array. Further on, such parameters may relate to chemical or physical properties of a material microneedles are composed of.

To this end the method according to the invention comprises the steps of:
  selecting a soft production mold comprising a set of microscopic incisions defining geometry of the microneedles, said soft production mold being capable of providing the microneedle array integrated into a base plate;
  using a filler material for abundantly filling the microscopic incisions of the soft production mold thereby producing the microneedle array with pre-defined geometry integrated into the base plate; wherein
  for the filler material a water or alcohol based ceramic or polymer-ceramic slurry is selected.

The technical measure of the invention is based on the insight that by using a suitable soft production mold fabrication of a microneedle array can be enabled, whereby microneedles are inherently integrated with the base plate. The resulting microneedles are porous due to the particular material choice for the filler. It is found that the intrinsic porosity of the microneedle array manufactured according to the invention can enable a suitable tuning of functionality of the microneedles, as the pores may be used as carriers of suitable chemical elements. Thus, porous materials of sufficient strength suitable to overcome a material barrier, such as skin, may advantageously add functional features to systems comprising microneedle arrays. In this respect the microneedles according to the invention solve a further problem of the art—a limited level of functionality of known solid microneedles.

The soft production mold can be produced beforehand in accordance with specific requirements which have to be met by the microneedle array. The soft production mold thereby defines the sought geometry and can be relatively easily produced by methods known in the art. For example, the soft production mold can be produced using per se known lithographic methods. The soft production mold is preferably fabricated from a pre-defined hard mold using an intermediate mold. Preferably, the intermediate mold is soft.

Additionally, the soft production mold can be formed to enable generation of optional microsized features, for example, channels, in microneedles by multilevel lithographic processes. In case of channels these may convey for suitable high substance transport throughout the base plate, for example, flow rates of at least 60 µl/h may be achieved.

Such soft-replica is an exact copy of the features produced in the hard mold with little or even no measurable change in dimension if polydimethylsiloxane (PDMS) is employed as the soft-lithography material. It has been known in the art that releasing a replica from a complex three-dimensional shape similar as delivered by the hard mold for microneedles introduced here, soft-lithography reproduction of the intermediated mold is more reliable (fault-free) and easier to perform than by releasing a hard-replica from a hard mold. This can be explained due to relaxation of forces in the flexible body of the replica during release. Basically, this way a soft-replica is peeled off the hard mold using shear forces instead of only using a one-directional pulling force as in the case of hard-replica processing. Although such soft-replica can be deformed during release it remains unaltered in its geometrical definition after recovery from the mold, especially when the material of the soft replica is elastic. The same reasoning applies for the copy process from the intermediate to the production mold as well as from the production mold to the green state of the final replicas delivering, after a drying process has been completed, the final integrated microneedle array structure. It will be appreciated that the replica realized by filling ceramic slurry into the production mold will lead to release of a replica in ceramic green-state, so called green tape.

In case when it is required to modify any of the geometric parameters of the microneedle array, like tip shape, diameter and/or length of individual microneedles, diameter and configuration of a channel in individual microneedle, position of a distal opening of the channel with respect to the tip, density of the microneedles in the array, etc., the soft production mold may be modified and the replication process can commence. In this way it suffices to change only the configuration of the soft production mold, while keeping the replication process unaltered.

An example of a direct replication process for microneedle arrays from a suitable hard mold utilizing a sacrificial release layer instead of flexible production molds is described in R. Luttge at al "Integrated lithographic molding for microneedle-based devices", Journal of Microelectromechanical systems, Vol. 16, No. 4, 2007. Although the fabrication of silicon hard molds in combination with direct SU-8 lithography as described in the aforementioned publication provides also microneedle arrays as a replication result the invention enclosed here reduces the process complexity of the hard mold, yielding a higher reliability in manufacture of the hard mold while increasing the flexibility for customized design changes. Further the invention here allows easy release from the production mold, i.e. no inconveniently long sacrificial etch step is required and no additional auxiliary features are required to allow such sacrificial layer etch. Further the replication process from the production mold as described in this invention is completely independent from a lithographic step, thus the replication step is also significantly simplified and suitable for very high volume production (mass production of devices). Altogether the advantages of the present invention significantly increase production yield for using the production mold in particularly in the replication of ceramic integrated microneedle arrays. Since the process area per production mold is limited by the originally used size of the silicon process, for example utilizing a silicon wafer with a 4 inch diameter, the production capacity can be increased by assembling a plurality of copies of the production mold into one replication matrices such as known in the art of very high volume manufacture (for example roll-to-roll processes).

In accordance with the invention replication is carried out preferably using the soft production mold, as it is found that ceramic or ceramic composite material in green state is more fragile than a common non-porous polymer material used in replication. A soft-mold further guarantees securely (fault-free high yield) release of a ceramic or ceramic composite green tape for the manufacture of a microneedle array integrated with the base plate from the production mold.

It will be appreciated that the term 'integrated' used in the context of the application means that the microneedle structures are inherently integrated with the base plate, i.e. they are formed during the same technological step. As a result, the step of assembling the individually manufactured microneedles with a separately manufactured base plate, as is known from US 2005/251088, is avoided. As a result the amount of relevant production steps of the thus produced microneedle array is reduced and therefore easier as well as less costly to implement in manufacture, while the intrinsic connection between microneedle and base plate additionally allows continuous transport characteristic throughout the entire microneedle array. These transport characteristic can be described and are of equally high tailorability as found in tortuous (porous) membranes known in the art of membrane technology.

Preferably, in order to further simplify removal of the fabricated microneedle array from the soft production mold, the method according to the invention comprises the step of coating a surface of the microscopic incisions of the soft production mold with an anti-adhesion layer. For example, Teflon or similar materials may be used for this purpose.

It is found that when for the filler material a water or alcohol based ceramic or a polymer-ceramic slurry is selected, a porous ceramic or polymer-ceramic microneedle array is produced. Such microneedle array may have superior physical properties when compared to a known polymer or porous polymer array. In particular the porous microneedle array as provided by the method according to the invention is more robust leading to a greater range of dimensions of the individual needles which are feasible compared to the known microneedle array and providing suitable strength to penetrate a material barrier such as, for example, skin. In addition, the microneedle array provided by the method of the invention due to its increased rigidity compared to porous polymer materials can be removed from the production mold without loss of geometrical definition as it is often observed, for example in phase separation processes utilizing polymeric replication materials only. The use of a ceramic composite in replication, instead of solely polymeric material, provides therefore a higher strength to the replica and thus a reduced rate of production faults. It is appreciate that one notes that the replica realized by filling ceramic slurry into the production mold will lead to the release of a replica in ceramic green-state, so called green tape. A green tape needs to undergo a distinct drying procedure to be converted to the full material strength as required to penetrate a material barrier such as, for example, skin. When the green tape is recovered from the soft production mold microneedle arrays can be customized in terms of sizing the extend of their base plate, for example, cutting sections from the green tape with the desired aerial dimensions of the patch according to the requirements of a distinct application.

In an embodiment of the method according to the invention, the method comprises the step of providing one or more microsized channels in the microneedles of the microneedle array for enabling transport of a substance through the one or more channels into the base plate or vice versa. Such channels may have dimensions in the order of 10-200 micrometer across at least one of its diameters, while its geometrical shape can be defined at will, for example, rectangular, triangular, round, elliptic etc.

For example, one or more projections in the microscopic incisions of the soft production mold may be provided for forming a fluid channel in one or more microneedles of the array for conducting a fluid there through.

In case when the microneedle array is conceived to be used for a delivery of a drug or for extraction of a body fluid or the like, it can be advantageous to provide the microneedle array with an additional fluid conduit next to the intrinsic porosity of the material. Although the use of porosity only may avoid certain conceived drawbacks of backpressure flows with microneedles containing such microsized flow channel. Configurations, however, will depend up on the specific use of such integrated microneedle arrays. Such conduit can be formed within the microneedle array at substantially any place. However, when such channel is formed within at least one of the microneedles a relative central positioning of the channel is preferred. Additionally, a plurality of protrusions may be provided in the microscopic incisions for forming respective channels in the microneedles. It will be appreciated that either a single channel per microneedle or a plurality of channels per microneedle are contemplated. In this way the microneedles may be used to administer a suitable drug or for extracting a body fluid achieving higher flow rates (for example inflicted by a suitable pumping mechanism applying vacuum or pressure) than it is possible by the resulting porosity of the material itself. In further relation to applications such flow channel can provide additional functionality as for example selective elution of a surface-captured substance. For example, elution processes may be utilized in analytical applications transferring the captured substance to an analytic device, for example a mass spectrometer. Channels may also be selected in areas of the base plate only. Such openings in the base plate may add to functionality of the system, for example when such systems need to be fixed to the skin.

In a further embodiment of the method according to the invention, the method comprises the step of forming respective end portions of the microscopic incisions on an oblique surface for forming the microneedle array with oblique tips.

It is found to be advantageous to suitably shape the soft production mold so that microneedles with oblique tips may be provided. Such microneedles may penetrate the material barrier, like skin, more easily. Such shaping may be enabled using specific crystallographic planes of a hard master mold, as will be discussed in more detail with reference to figures.

In a further embodiment of the method according to the invention, the method further comprises the step of adaptively modifying properties of the filler material by supplementing the filler material with an additive.

As a result, it is possible to tailor properties of the microneedle array by changing characteristics of the filler material. By using an additive for modifying properties of the ceramic or ceramic composite microneedles, the microneedle array produced according to the method of the invention can have application-tailorable meso-and macroporosity, specificity of sorption characteristic and tunable interfacial transport. In the manufacture enclosed here the example of adding Kaolin is presented. A broad variety of such additives may be envisaged delivering nanoscale-defined hybrid materials, incorporating carbon nanotubes, quantum dots, nanoshell particles either with or without a core of either organic or inorganic nature. For example, nanosized particles of metallic or inorganic nature may be added to the slurry. Further such tailoring may be carried out in a post-replication step, modifying the green-state by dispensing according substances onto the array. These modifications may change overall characteristics of the array material, but may also be seen as an opportunity to introduce different modifiers to the material by localized dispensing of such suitable additive. Suitable precision liquid dispensing techniques are known in the art. For example, such application-tailorable properties may be adapted for performing administration of a drug or for diagnostic purposes. Therefore, the method according to the invention provides a relatively inexpensive solution for mass production of microneedle arrays for a great plurality of application. The thus produced microneedle arrays can be used not only for drug delivery or for extraction of a portion of a body fluid, but they can also form part of an electrode, used for example for myo-stimulation, detection and/or monitoring of an electrical signal reflective of a vital sign, like EEG, myometry, cardiac activity.

In an embodiment of the method according to the invention for the ceramic slurry alumina, zirconia or hydroxyapatite may be selected.

It is found to be advantageous to use these slurries because the mold can be filled with it quite accurately and the shapes of the formed microneedles can be easily recovered from the mold. It is further found that physical properties of the ceramic microneedle array, like porosity may be easily tuned when a suitable amount of an additive, such as Kaolin, is added to the original slurry. It is found that trace amount of a suitable Si-comprising mineral, like Kaolin may be added to the original slurry. Due to the fact that Kaolin mainly comprises silica, envisaged slurry, for example, silica-alumina nano-composite slurry, creates an interface which results in a mechanically stronger material, because subcrystalline boundaries are created within the bulk of the material but also favorably modifies the properties of the green tape, which allows to securely recover the green tape from the production mold. It is found that when Kaolin is added the sintered ceramic demonstrates a large transcrystalline fracture behavior, which means that it has a stronger grain-boundary than pure alumina resulting in a stronger ceramic.

In a further embodiment of the method according to the invention the soft production mold is manufactured using a double replication of a hard master mold via an intermediate soft mold.

Using such double replication process has an advantage that for purposes of tailoring geometry of the microneedle array the master mold may be changed leading to a modified soft replication mold, wherein the replication process from the soft replication mold to the microneedle array stays unchanged. Thus, once the manufacturing, i.e. replication, technology is optimized it may be kept optimal irrespective of specific geometric demands of the microneedle array.

Accordingly, it is possible that the hard master mold is first replicated into a suitable plurality of soft production molds which may be disposed of upon use. This has an advantage that the geometry of the microneedle array defined in the master mold is readily replicable in a great number of end products without distorting the initial geometry of the master mold due to repetitive use thereof. Preferably, the material of the soft replication mold is elastic. This is advantageous, as elastic material induces less tension on the microneedle array when it is removed from the mold, thereby reducing production losses and improving quality of the thus produced ceramic or ceramic composite microneedle array.

In a still further embodiment of the method according to the invention the method further comprises the step of manufacturing the hard master mold using the steps of:

disposing a first layer of a radiation sensitive material on a working surface of a Si-wafer coated with a masking layer;

processing the first layer by means of lithography for forming first openings in the masking layer cooperating with pre-determined crystallographic planes in the Si-wafer, said openings having pitch and width;

etching the masking layer for forming second openings cooperating with the first openings;

forming a set of cavities in the Si-wafer cooperating with the second openings;

filling the set of cavities in the Si-wafer with a layer of photoresist;

generating a set of inverted microneedles in the layer of the photoresist.

It will be appreciated that the openings in the Si-wafer may be generated using a suitable lithographic mask. As a result, a new sequence of technological steps is provided which enables simple means of changing systematically the tip shape, diameter, the length of a single needle as well as array density by modifying the planar mask design in the photolithographic steps during fabrication of the hard soft molds (i.e. the intermediate and the production mold) and the replication process from the production mold to the ceramic integrated microneedle array remain unaltered. It will be appreciated that the step of generating inverted microneedles may be carried out using lithography comprising the steps of overlaying the openings with a suitable mask corresponding to a desired shape of the microneedles, exposing and developing the photoresist present in the cavities thereby yielding the inverted microneedles having pitch and width related to the pitch and width of the openings. It will be appreciated that when all cavities are used for forming similar sub-sets of microneedles, the pitch of the sub-sets of microneedles may be equal to the pitch of the openings used to create the cavities. However, it is also possible that not all cavities are used for forming the microneedles, in this case the pitch of the sub-sets of the microneedles may suitably relate to the pitch of the openings. Usually, it may be preferred to select the pitch of the sub-sets of the microneedles to follow the pitch of the cavities, however, for example, when sub-sets of four microneedles per cavity are generates (see FIG. 7), than the pitch between the individual microneedles in the sub-set is different than the pitch of the openings.

Optionally, a multilevel process can be performed by dispensing an additional photoresist layer on the first exposed layer prior to development, yielding for example additional protrusions in the hard mold after development. Such step may be utilized, for example, to form a microsized channel in the microneedle array.

Preferably for the masking layer used for protection of the silicon wafer during anisotropic etching a Silicon Nitride layer is used. In the method according to the invention for etching of the masking layer reactive ion etching may be used. In addition, the set of cavities in the silicon (also refereed to as grooves, pyramidal pits) may be formed using anisotropic wet etching of the silicon using KOH. As in the example described here the silicon (100)-working surface is processed, in which the fast etching 100-plane is etched selectively against 111-planes. As it is known in the art 111-planes will define the shape of the anisotropically etched cavity, here, in a pyramidal pit. In the method of the invention, a thickness of the photoresist layer filling the said structures (here pyramidal pits as means of example, generating a pre-patterned working surface for the subsequent lithography processes) is selected to determine a length of the resulting microneedles. Also, the method of the invention may comprise the step of modifying the pre-patterned working surface in silicon using an anti-reflection layer prior to dispensing the thick-layer photoresist. Due to this feature ghosting effects in the subsequent lithography steps resulting from multiple reflections from the oblique surfaces in the pits may be eliminated. Commonly, polymeric layers are known as anti-reflection layers matching SU-8 lithography. However, such polymeric layer for example, dispensed by spraying or spinning, will lead to modify the geometrical precision of the pits. A thin-film-type modification of the working surface is therefore preferred, when subsequent lithography is carried out on a pre-patterned working surface. A suitable thin-film modifier of the said reflection properties may relate to a thin-film titanium silicide layer, which may be processed at about 700° C. in nitrogen flow.

Use of lithographic techniques is preferable, because such method is relatively cheap and enables production of microscopic surfaces with well defined features, like wall slope, well dimension and the like. Preferably, the first layer of radiation sensitive material forming part of the hard-mold is processed by means of selective irradiation thereby suitably patterning the first layer. It is also possible that complementary to the first layer a second radiosensitive layer is provided. In this case the method may further comprise the steps of processing the second layer of the material for forming at least one channel in the microneedles. Such processing is preferably carried out by means of UV-lithography into SU-8 photoresist. With respect to lithographic methods a variety of suitable radiation sources is contemplated. For example, it is possible to use an electromagnetic source, for example a source generating visible light, (deep) ultra-violet light or even x-ray light, whereas photoresist chemistry has to be chosen accordingly.

It is possible to selectively irradiate the first layer of material, to provide a second layer of a material on the selectively irradiated first layer of material and to process the second layer of the material together with areas of selective irradiation of the first layer for forming at least one channel in the microneedle array. In this way a suitable feature may be formed in a non-irradiated area of the first layer, within the selective irradiation step of the second layer, where after the second irradiating step of the features in the first layer will be developed together with the features in the second layer thus forming together parts of the hard-mold. This is advantageous, because it takes less process steps and can easily be implemented thereby saving processing time.

It will be appreciated that a method is described with reference to a negative resist. In case when for the radiation sensitive material a positive resist is selected, the respective areas will be inverted so that portions which are processed will define suitable features of the microneedle array. By virtue of terminology the negative resist relates to a radiosensitive material which solubility in a suitable etchant decreases post illumination. A positive resist relates to a radiosensitive material which solubility increases post illumination.

In a particular embodiment of the method according to the invention the light source used for lithography may be disposed in such a way through an according mask (for example a chromium-on-quartz photolithography mask in UV lithography) as to process the first and/or the second layer for forming the hard-mold containing the inverted shape of a microneedle array either provided flat or with oblique tips. The embodiment of the microneedle array consisting oblique tips is particularly suitable for improving a penetration of the microneedles through a material barrier, for example through a skin barrier. Due to the fact that the tips are oblique with respect a surface of the barrier is being cut on a microscopic scale. This is advantageous with respect to a tensile penetration of a flat tipped microneedle array because in the former reduced skin damage is induced.

It will be appreciated that although examples of specific technological processes are named, such examples may not be construed as limitation, as a plurality of equivalent or substantially equivalent material processing methods may be applied. Alternatively, in the case of using x-rays PMMA (polymethyl-metacrylate) may be applied as a radiosensitive layer.

The microneedle array according to the invention comprises a base plate and a set of microneedles integrated with the base plate, wherein the microneedles comprise a porous ceramic material or a porous ceramic composite material, for example polymer-ceramic or metal-ceramic composite.

It will be appreciated that the term 'composite' may relate to a composition comprising at least two elements, whereby one of the said at least two elements may be present as a trace element. In particular, a ceramic material provided with suitable additives for tailoring its properties is regarded as a composite ceramic, irrespective of the weight fraction of said additives. Similar to the example using Kaolin other organic or inorganic materials may be used to alter the properties of the green-state as well as the final material of the integrated microneedle array. One can envisage adding silver or iron, or iron-oxide particles to the slurry tailoring properties of conductivity of magnetizing capabilities within the final device.

Preferably, the microneedle array is fabricated by the method as is set forth in the foregoing. The microneedle array according to the invention comprises porous microneedles which are yet robust improving their useful properties. For example, the pore size may be selected in the range of sub-nanometer to several nanometers for a microneedle having a length of several tens of micrometers, preferably in the range of 100 to 550 micrometers. In addition, the porous ceramic or ceramic composite microneedles may have porosity in the range of 10-45%. Pore diameter of 20-200 nm can easily be achieved—so meso- and macroporous materials can be made (when nanocrystalline, e.g. zirconia, powders are used pore diameters of 10 nm are possible).

Such microneedles may be used to produce suitable skin patches with improved quality. It is found that use of additives in the ceramic microneedle yielding a ceramic composite microneedle having particle size in the nanometer range improves surface qualities of the microneedles, because surface properties of such microneedles which pores are at least partially filled with nano-meter material are substantially improved simplifying protrusion of the microneedle array through a skin barrier. Such microneedles are preferable for suiting demands of diagnostics or therapy.

In a particular embodiment of the microneedle array according to the invention said set of microneedles comprises microneedles of different lengths. This may be advantageous when different microneedles have to penetrate to a different depth, or, when the longer microneedles are used to pre-stretch the skin prior to penetration of shorter microneedles. The shorter microneedles may be drug carrying, or passive for extracting a body fluid or for providing an electrical contact with the body. In the latter case it is preferable that the microneedles comprise or are coated with an electrically conducting material, for example Ag.

It is found to be advantageous when said plurality of microneedles comprises at least a first and a second microneedle being arranged substantially opposite to each other on a periphery of said set, wherein said at least the first and the second microneedles have increased length with respect to overall microneedles of said set.

Such configuration is used to pre-stretch the skin before the shorter microneedles enter the skin barrier. It is further possible that the longer microneedles located at the periphery have a different, for example greater, cross-section than the shorter microneedles. This may improve pre-stretching of the skin. Preferably, the microneedle array according to the invention comprises microneedles with the aspect ration in the range of 3-6, whereby the length of said at least the first and the second microneedles is at least 1-10% larger than the length of the overall microneedles of the set. Larger differences, of course, can be also achieved, as for example when flat-tips being produced onto the plane area of the silicon working surface are combined with the oblique tips resulting from the overlay with the pits in the silicon working surface. Additionally or alternatively, the microneedles are formed with oblique end surfaces conceived to interact with a material barrier. With this geometry penetration through a material barrier, for example the skin, is further improved. It will be appreciated that the oblique surfaces of such elongated microneedles may be facing each other, or may be opposed to each other.

A system for transporting substances across a material barrier according to the invention comprises a microneedle array according to the fore going.

A system for extracting or for injecting a fluid according to the invention comprises a microneedle array according to the foregoing.

A system for measuring an electric signal using an electrode according to the invention comprises an electrode formed at least partially from a microneedle array as discussed in the foregoing. Such system may be used for recording of an electrical signal representative of a physiological parameter. For example, such system may be used for recording or long-term monitoring of EEG signal, signal related to cardiac activity, myographic signal, or the like. Recording to the EEG using methods known in the art is time consuming, in particular regarding mounting of the electrodes and skin preparation. An electrode comprising a microneedle array, as is discussed with reference to the foregoing, substantially reduces the mounting time and circumvents the need for skin preparation, in particular removal of part of the epidermis by scrubbing.

It has been demonstrated that the signal-to-noise ratio of the microneedle-based electrodes used for receiving an electric signal related to a vital sign is substantially the same as the signal-to-noise ration of the conventionally used macroscopic electrodes. Therefore, there is substantially no trade-off between the reduction of the mounting and preparation time and resulting quality of the collected signal, making such system advantageous for investigating and/or monitoring of a vital sign of adults and neonates. The system may provide in a further embodiment the use of such microneedle array comprising electrodes for in-home environment patient monitoring.

These and other aspects of the invention will be further discussed with reference to drawings. It will be appreciated that the drawings are hereby presented for illustrative purposes only and may not be used for limiting the scope of the appended claims.

BRIEF DESCRIPTION OF THE DRAWINGS

FIG. 1c presents an embodiment of a resulting cut into a skin model system obtainable with the microneedle array of FIG. 1a.

FIG. 2 is a schematic cross-section view of a wafer coated with a thin layer of Silicon Nitride that may be used in the construction of the skin patch of FIG. 1;

FIG. 3 is a schematic cross-sectional view of the wafer of FIG. 2 with a layer of radiation sensitive material coating the layer of Silicon Nitride;

FIG. 4 is a schematic cross-sectional view of the wafer of FIG. 3 with a patterned radiation sensitive material;

FIG. 5 is a schematic cross-sectional view of the wafer of FIG. 4 post etching, wherein an array of openings in the Silicon Nitride layer is created;

FIG. 6 is a schematic cross-sectional view of the wafer of FIG. 5 after wet etching for creating grooves or pits therein according to the arrayed openings in the Silicon Nitride layer.

FIG. 7 is a schematic isometric view of the wafer of FIG. 6 depicting a detail A-A.

FIG. 8 is a further schematic cross-section view of the wafer of FIG. 7.

FIG. 11a is a schematic cross-section view of the wafer of FIG. 10 after dispensing, overlay, exposing a second layer of photoresist;

FIG. 11b is a schematic cross section view of the wafer of FIG. 10 processed according to FIG. 11a, yielding a hard-mold with additional protrusions, for forming flow channel across a microneedle extending into the base plate.

FIG. 11c is a schematic cross section view of the wafer of FIG. 10 filled with PDMS.

FIG. 14 is a schematic cross-section view of a further embodiment of a wafer;

FIG. 15 is a schematic cross-section view of a still further embodiment of a wafer;

FIG. 16 is a schematic cross-section of a released production mold.

FIG. 17 is a schematic cross-section of a production mold covered with an anti-adhesive layer.

FIG. 18 is a schematic cross-section of a production mold filled with a filler material.

FIG. 19 is a schematic cross-section of a micro-needle array.

FIG. 20 is a schematic view of a functionalization step.

DETAILED DESCRIPTION OF THE DRAWINGS

Figure 1:
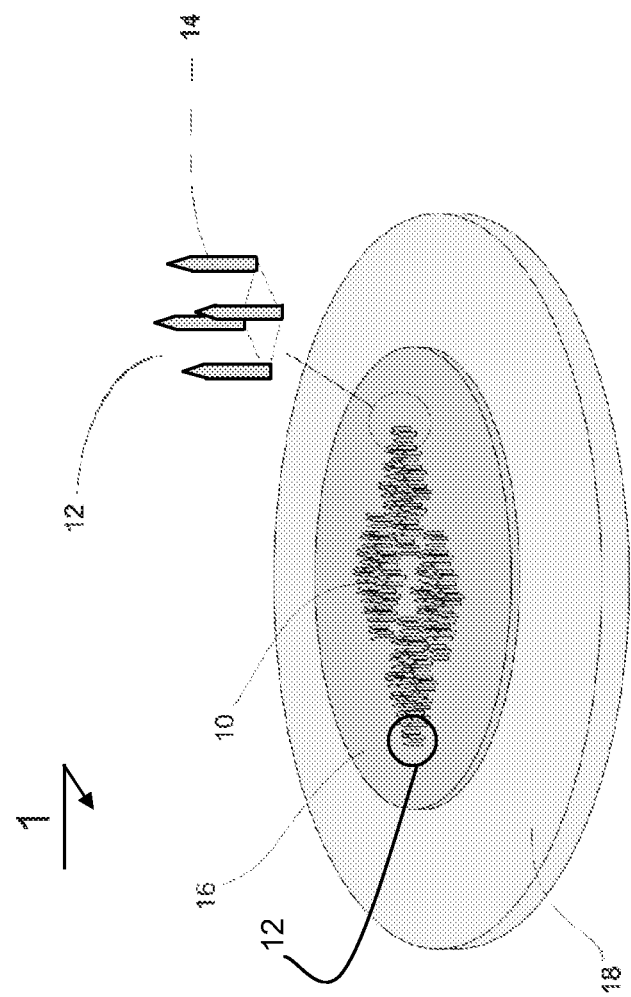
FIG. 1 is a schematic isometric view of a nano-material embedded skin patch in accordance with a preferred embodiment of the present invention.

FIG. 1 is a schematic isometric view of a skin patch using a microneedle array in accordance with a preferred embodiment of the present invention. The skin patch 1 comprises a platform for placing and, preferably, fixating the skin patch 1 to the skin. The platform 18 is preferably manufactured from a biocompatible material, which may be arranged breathable for ensuring durable application of the skin patch on the skin. This may be advantageous in case when the skin patch 1 is conceived to be used as electrodes for conducting EEG, myography or any other suitable electric interaction with the skin.

The skin patch 1 further comprises a set of preferably arrayed out-of-plane microneedles 16 inherently integrated with the base plate. In accordance with the invention the microneedles 16 comprise porous ceramic or porous ceramic composite material, for example polymer-ceramic material. The microneedles 16 may be provided with a substance conceived to be transported through a skin barrier or with a substance having a specific binding with a further substance conceived to be extracted through the skin barrier. Such substance may be a protein or other molecule, or molecular complex, including architectures based on liposome or polyelectrolyte chemistry suitable for therapeutic treatment and targeting. On the other hand such compound can interact with compounds in the body fluid, for example for the selective binding of a specific protein which has been identified as a biomarker.

It is possible that the array of microneedles 16 comprises sub-regions having different functionality. For example, the sub-region 10 may be eventually arranged with increased or decreased porosity in relation to the overall microneedles of the array 16. Such porosity modulation may be performed during a later processing step, for example during functionalization, as described with reference to FIG. 20. Preferably, the microneedle array 16 comprises a suitable plurality of elongated microneedles 12 for simplifying skin penetration, as it has been found that by providing such elongated microneedles the skin is pre-stretched prior to it being at least partially protruded by the overall microneedles.

It will be appreciated that according to the invention the microneedles array may be limited to a set 12, formed in a cavity of a Si-wafer. In addition, in accordance with the invention, a wide range of specific arrangements of the microneedle tips is feasible. For example, the microneedles, forming a set 12 may have tips oriented upwardly. Secondly, the tips may be formed obliquely either facing each other or being oriented outwardly from adjacent microneedle tips forming the set 12. Usually the set 12 comprises 4 microneedles. Such grouping is referred to as a sub-set. As has been explained earlier, a pitch between the sub-groups 12 of the microneedle array may correspond to the pitch of the openings in a mask used for forming respective cavities in the Si-wafer. The pitch between the microneedles of the sub-set is a fraction of the pitch between the sub-sets. Preferably, the microneedles forming the sub-set are arranged to be substantially symmetrically distributed over the cavity in the Si-wafer. More details on the possible arrangements of the microneedles will be discussed with reference to FIGS. 1a-1c.

Preferably, a sub-set of elongated microneedles is arranged at periphery of the array 16, notably diametrically dislocated from each other. In addition, the array 16 may comprise one or more microneedles 14 of distinguished geometry, that is of a geometry which may be substantially different from the geometry of the overall microneedles of the array 16. This may be advantageous in cases when such one or more microneedles 14 have a different purpose than the overall microneedles. For example, delivery of different vaccines or sampling at different time intervals.

Figure 1A:
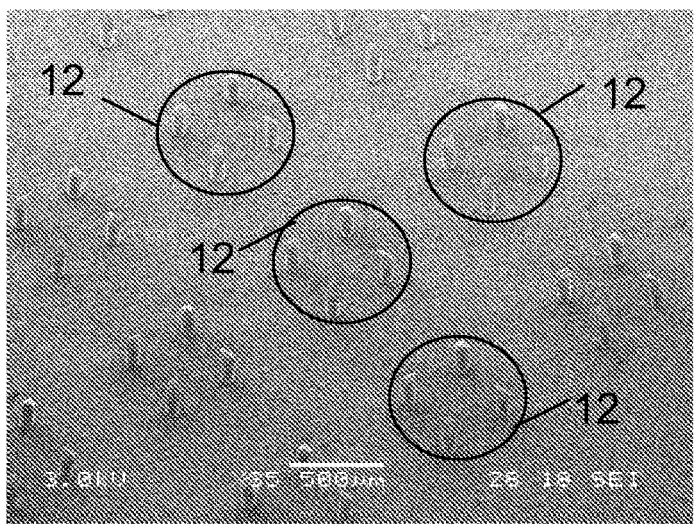
FIG. 1a presents a scanning electron micrograph of a microneedle array configuration.

FIG. 1a presents a scanning electron micrograph of a microneedle array configuration. In this particular embodiment, one of the possible microneedle array configurations is shown depicting groups of microneedles 12 having oblique end surfaces pointing inwardly. It will be appreciated that the hard mold design may be suitably altered for providing microneedles with oblique tips pointing outwardly. However, it is also possible to design a mask for providing microneedles array wherein individual microneedles comprise tip shapes of different configuration. Generally, such arrangement is advantageous for microneedle arrays wherein individual microneedles have different purpose. For example, when some microneedles are used for cutting the skin and the other microneedles are used for transporting of a substance across the skin, both injecting and extracting being contemplated.

Figure 1B:
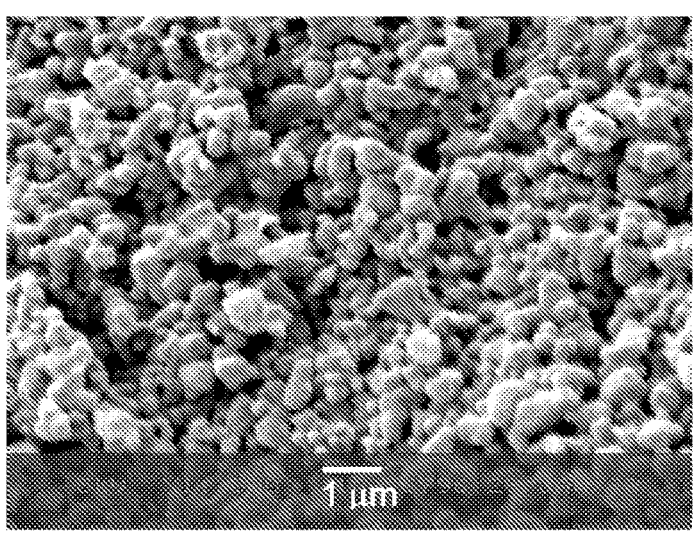
FIG. 1b presents a scanning electron micrograph depict porosity of a ceramic microneedle array provided with the method of the invention.
Figure 1C:
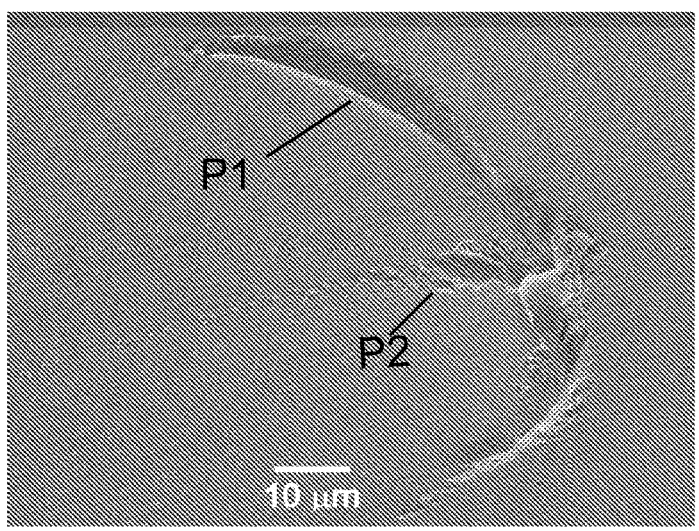

It will be appreciated that although the scale of FIG. 1a is 500 micrometer in 1.4 cm of the picture, no particular limitation on the microneedle sizing may be inferred. FIG. 1b further shows a detail of the intrinsic porosity of the alumina filler after drying, recovery from the soft production mold and sintering at high temperature. In this particular embodiment, which is presented with a considerably higher magnification than that of FIG. 1a, trace amounts of Kaolin have been added to the ceramic slurry. FIG. 1c presents an embodiment of a resulting cut into a skin model system obtainable with the microneedle array of FIG. 1a. FIG. 1c depicts with a considerably higher magnification as shown in FIG. 1a the penetration marks P1, P2 post microneedle insertion into a skin model system, wherein the microneedle array configuration relates to a set of 4 microneedles, depicted by 12 in FIG. 1a. In this example an elastomer (PDMS) has been used to mimic the skin reaction. The marks P1, P2 are at microscale and refer to the penetration marks similar to the small insertion wounds that would be generated when the microneedle array is used to penetrate human skin. It is seen that these marks are smaller and smoother that the cutting marks obtainable with conventional flat tips. Such tip configuration wherein tips of the microneedles are oblique and several microneedles work together in a small group 12 during insertion is preferable for skin penetration in medical applications. In this respect inward or outward orientation is preferable than arbitrary or one-sided orientation.

FIG. 2 is a schematic cross-section view of a Si wafer 20 coated with a Silicon Nitride layer 22 which may be used in the fabrication of a hard mold for providing a soft production mold for producing the skin patch of FIG. 1.

In accordance with the method of the invention a silicon wafer 20 is selected for providing a working surface for forming a hard master mold. The silicon wafer 20 is coated with silicon nitride thin-film coating, which may be used as a masking layer. FIG. 3 is a schematic cross-sectional view of the wafer of FIG. 2 with a layer of radiation sensitive material 24 coating the layer of Silicon Nitride. The radiation sensitive layer 24 is preferably suitable for performing ultra-violet lithography.

FIG. 4 is a schematic cross-sectional view of the Si wafer 20 of FIG. 3 with a patterned radiation sensitive material 24 after a suitable lithographic step has been performed. It is seen that openings 26 are formed in the radiation sensitive layer 24 for selectively removing silicon nitride layer 22. FIG. 5 is a schematic cross-sectional view of the Si wafer 20 of FIG. 4 post etching, wherein an array of openings 26 in the silicon nitride layer 26 is created. Preferably, for this purpose reactive ion etching is used. It will be appreciated that the openings are provided at places spatially matching (aligned) with specific orientation of crystalplanes of the Si-wafer, like (100). From the crystallography it follows that such openings will yield specific structures (for example, pyramidal pits determined by the selective etching of the 100 and the 111 planes in the silicon) have a pre-defined pitch and width, which may define the resulting geometry of the microneedle array. It will be appreciated that the technology of alignment of the mask with the internal structures is known per se, for example such alignment may be carried out using microscope-augmented mask alignment between a standardized silicon wafer and a chromium mask layout).

FIG. 6 is a schematic cross-sectional view of the wafer 20 of FIG. 5 after wet etching for creating grooves 30 or pits therein according to the arrayed openings 26 in the silicon nitride layer 28, shown in FIG. 5. Preferably an anisotropic wet etching using potassium hydroxide KOH is used.

FIG. 7 is a schematic isometric view of the wafer of FIG. 6 depicting a detail A-A running through a two-dimensional image of the wafer 32. It is seen that grooves 30 having dimension (x, y) are spaced in the wafer having respective pitches in x-direction $P_x$ and y-direction $P_y$, which may correspond to the pitch of the internal structures of the Si wafer. The properties of thus formed grooved surface (pre-patterned silicon working surface) may be modified by using an anti-reflection layer 34 (see FIG. 8). The anti-reflection layer 34 serves to mitigate ghost features occurring during lithography, which advantageously improved geometric properties of the microneedle array. Preferably, for the anti-reflection layer titanium silicide is used.

Figure 9:
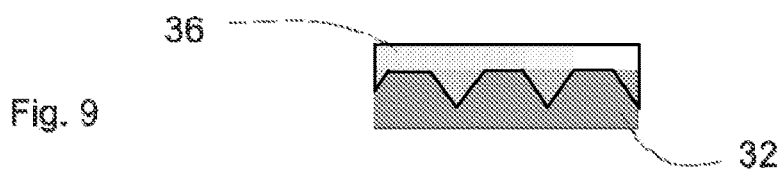
FIG. 9 is a schematic cross-section view of the wafer of FIG. 8 having a thick layer of photoresist spin-coated thereon.

FIG. 9 is a schematic cross-section view of the wafer of FIG. 8 having a layer of photoresist 36 spin-coated thereon. Preferably, the layer of photoresist has a thickness in the range of 50-360 micrometers measured from a planner plane of the working surface, whereby for the resist conventional SU-8 100 material is used. The thickness of the photoresist material 36 determines the length of the resulting microneedle array.

Figure 10:
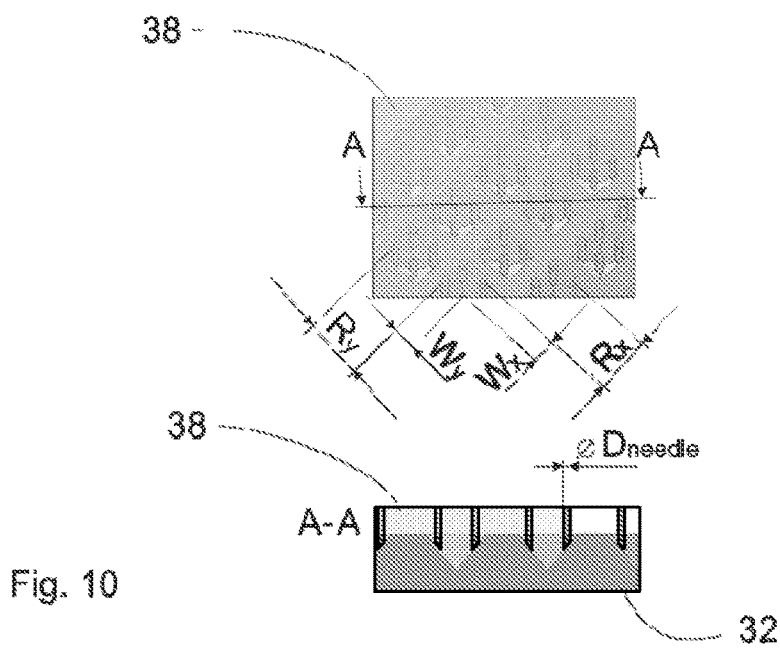
FIG. 10 is a schematic isometric view of the wafer of FIG. 9 showing an embodiment of a layout of the microneedle array by referring to the detail A-A.

FIG. 10 is a schematic isometric view of the wafer of FIG. 9 showing an embodiment of a layout of the microneedle array by referring to the detail A-A. Exposed resist 38 shows a latent image of the inverted microneedles arranged in a pre-determined geometry having pitch parameters $R_x$, $R_y$, and width parameters $W_x$, $W_y$, which corresponds to the pitch and width of internal structures of the Si wafer used for manufacturing of the hard master mold.

Figure 11:
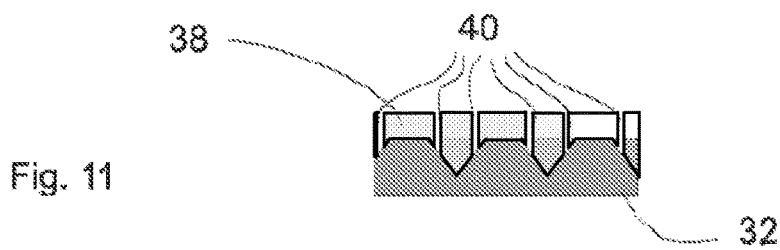
FIG. 11 is a schematic cross-sectional view of the wafer of FIG. 10 after selectively irradiation and developing of the thick layer of photoresist, defining a form of inverted microneedle structures.

FIG. 11 is a schematic cross-sectional view of the wafer of FIG. 10 after selectively irradiation and developing of the layer of photoresist 36 yielding exposed resist 38, defining a form of inverted microneedle structures as openings 40 in the exposed resist 38. In the context of the present application this structure is referred to as a hard master mold.

In accordance with a further embodiment of the method according to the invention, the hard master mold depicted in FIG. 11 is replicated twice for yielding a soft production mold which is used for manufacturing ceramic or ceramic composite microneedles inherently integrated into a base plate.

FIG. 11a is a schematic cross-section view of the wafer of FIG. 10 after dispensing, overlay, exposing a second layer of photoresist 70 through a mask 69. The photoresist 70 may be subsequently developed together with the first layer 38 that had been previously selectively exposed. FIG. 11b is a schematic cross section view of the wafer of FIG. 10 processed according to FIG. 11a post development, delivering a hard-mold with additional protrusions 71, which form respective microsized flow channels across a microneedle extending into the base plate. FIG. 11c is a schematic cross section view of the wafer of FIG. 10 processed according to FIG. 11a and FIG. 11b subsequently filled with PDMS for generating the soft intermediate mold 72. For clarity only a portion of the filling is drawn. Detail Y further depicts the copy from intermediate mold 72 and recovery of the soft production mold 73 containing a protrusion within the inverted shape of a microneedle. Subsequently, the ceramic filler is dispensed on the production mold 73, and the ceramic green tape 74, showing the flow-through channel in the microneedle and the base plate, is recovered from the production mold 73. For clarity only portions of the microneedle array are drawn in FIGS. 11a-11c.

Figure 12:
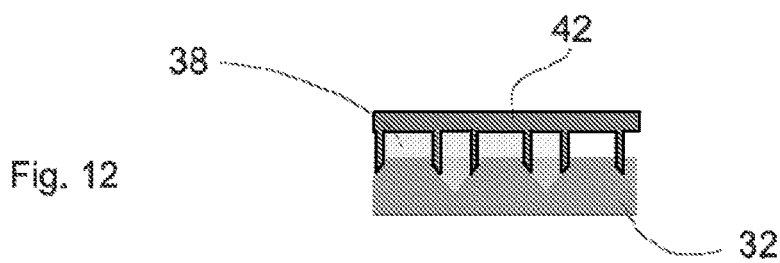
FIG. 12 is a schematic cross-sectional view of a wafer having an inverted microneedle structure disposed thereon.

FIG. 12 is a schematic cross-sectional view of the wafer 32 and exposed resist 38, openings of which are filled with a suitable filler material 42 for yielding an intermediate soft mold replicating the geometry of the hard master mold. Preferably for the filler material PDMS is selected to provide a flexible intermediate mold.

Figure 13:
FIG. 13 is a schematic cross-sectional view of the replicated soft-mold defining the shape of the microneedles.

FIG. 13 is a schematic cross-sectional view of the intermediate soft mold 42 having the exact shape of the microneedles corresponding to the geometry of the master mold shown in FIG. 11. It will be appreciated that replication process is known per se in the art and will not be explained here in detail.

FIG. 14 is a schematic cross-section view of a further embodiment of the intermediate mold provided with an anti-adhesion layer 44. This is found to be advantageous for simplifying release of the production mold which is formed using the intermediate mold.

FIG. 15 is a schematic cross-section view of a view depicting the soft production mold provided using a filling material 46 arranged on the intermediate mold. Preferably, also for the filling material forming the production mold PDMS is selected for yielding a flexible, preferably elastic production mold.

FIG. 16 is a schematic cross-section of a released soft production mold 46, which may be covered with an anti-adhesive layer 48, as is depicted in FIG. 17. Use of the anti-adhesive layer may facilitate an easy removal of the ceramic or ceramic composite microneedle array from the soft production mold.

FIG. 18 is a schematic cross-section of the soft production mold 46a filled with a filler material 50. The filler material 50 is provided in abundance thereby enabling formation of the microneedle array inherently integrated with a base plate in a single manufacturing step. In accordance with the invention for the filler material 50 a water or alcohol based ceramic or polymer-ceramic slurry is selected. It is possible to use alumina, zirconia or hydroxyapatite for yielding nanocomposite or nanohybride filler material. The slurry may contain metal particles or other additives for imparting additional functionality.

By way of example, a slurry to be used as the filler material may be provided as follows. Alcohol based polymer-precursor solution with additives is prepared. Hereby a polymeric binder, for example polyvinylbutural, is used in desired amounts and molecular weight apt to tailor the porous structure of final material. Subsequently ceramic powder with, for example, approx. 300-500 nm grain size in case of alumina is added to the binder solution. Using other material systems, for example zirconia, the grain size range can be around 50 nm or even smaller. A range of 0.5-7% of additives can be introduced, for example natural occurring oils, which enhance green tape properties and release behavior and particles of minerals, preferably having a diameter being 5-30% smaller than the main used ceramic compound. The additional mineral motivates the diffusion properties at the ceramic grain boundaries during sintering.

Regarding mineral additives, it is found that by adding at least of 0.1 Wt % of Si to the original slurry improved robustness of the final microneedle array yet preserving its porosity. With slurry having approximately 1 Wt % of Si inside of the material after sintering a still better result is achieved. It is found that advantageously the Si-based additive should be about 0.1-10 Wt % of the slurry, preferably about several weight percents, more preferably about 1 Wt %. Therefore, this tuning of the physical properties of the ceramic material offers functionalization of the microneedle array in the sense that its properties may easily be tailored for a specific envisaged application. Similarly, metals may be used as additives.

FIG. 19 is a schematic cross-section of a resulting microneedle array 50 integrated in a base plate and having porous structure, as depicted in detail X. Preferably, the filler material is supplemented with one or more additives for suitably tailoring properties of the microneedles as is explained in the foregoing. Preferably, for the additive a silica-based mineral, by means of example, Kaolin is selected. Hence, a such received integrated microneedle array in its green-state subsequently undergoes an according drying procedure, which may include step-wise application of a temperature profile up to very high temperatures known in the art of ceramic sintering, giving the material its final properties.

FIG. 20 is a schematic view of a functionalization step. Chemical or physical properties of a microneedle array 50 comprising a ceramic or a ceramic composite material may be advantageously tuned on demand by means of a functionalization step using an additive. For this purpose a surface of the microneedles may be coated with a suitable coating 54, 56 supplied from a suitable source 52. The suitable coating may be deposited as a monolayer, or, alternatively it may be deposited as a thin layer, having thickness in the range of a few nanometers. Sections of the array, for example individual microneedles of the array, may be modified selectively. Further, for example, the coating 54, 56 may comprise specific molecules, like pyrene for enabling specific binding characteristics. Alternatively, or additionally the coating molecules may relate to surface immobilized molecules. It will be appreciated that functionalization may be achieved not only by coating, but also by providing a substance conceived to at least partially fill the pores in the microneedles. Such substance may relate to a drug, or to another matter, for example to change hydrophilic or hydrophobic surface properties of the microneedle array by changing the surface charge of the hydrophilic alumina, e.g. applying titanium oxide formed, for example, from a sol-gel. Other example may be the modification of surface properties by liposome or polyelectrolyte chemistry capable of incorporating selective molecules suitable for specific targeting or increased bioavailability. Polyelectrolytes may incorporate molecules by click-chemistry.

It will further be appreciated that the method according to the invention is also applicable to fabrication of polymer microneedle arrays, wherein instead of alcohol based ceramic or polymer-ceramic slurry a polymer material is selected. As a result, a new technological sequence is provided for mass production of polymer microneedle arrays wherein said production sequence is relatively cheap and provides microneedles with tunable properties. For example, at least the following properties may be alterable on demand: tip shape or arrangements of a variety of tip shapes within one array, diameter of the microneedles, their length, density in the array, orientation of the oblique tips with respect to each other.

While embodiments of the invention disclosed herein are presently considered to be preferred, various changes and modifications can be made without departing from the scope of the invention. Those skilled in the art will appreciate that the figures show a limited number of microneedles in an array. However, a large number of microneedles per array arranges in different spatial configurations may be used. The scope of the invention is indicated in the appended claims, and all changes that come within the meaning and range of equivalents are intended to be embraced therein.

What is claimed is:

1. A microneedle array comprising:
   a base plate; and
   a set of microneedles integrated with the base plate,
   wherein the set of microneedles and the base plate comprise a porous ceramic material or a porous ceramic composite material having pores,
   wherein the set of microneedles and the base plate comprise the same porous ceramic material,
   wherein the diameter of the pores ranges from 10 to 200 nanometer,
   wherein the set of microneedles and the base plate are formed together during a single technological step so that the set of microneedles substantially seamlessly transit into the base plate, and
   wherein each microneedle of the set of microneedles comprises a tip that is defined by at least one oblique plane passing through the microneedle,
   wherein the set of microneedles comprise alumina particles having a grain size of 300-500 nm or zirconia particles having a grain size of 50 nm or less; and
   wherein the alumina particles or the zirconia particles are sintered together to form the porous ceramic material or the porous ceramic composite material having pores.

2. The microneedle array according to claim 1 wherein two or more microneedles in the set of microneedles have tip shapes of different configuration.

3. The microneedle array according to claim 1, wherein at least one microneedle comprises a channel for conducting a fluid therethrough.

4. A composition comprising a microneedle array according to claim 1, wherein said composition comprises a substance conceived to be transported through a material barrier or conceived to have a specific binding to a further substance to be extracted via the material barrier using the set of microneedles.

5. The composition according to claim 4, wherein the set of microneedles comprises pores at least partially filled with the substance.

6. A system for enabling transport of a substance through a material barrier comprising a microneedle array according to claim 1.

7. A system for measuring an electric signal using an electrode, wherein the electrode comprises of at least one of the microneedles in the microneedle array according to claim 1.

8. A microneedle array comprising:
   a base plate; and
   a set of microneedles integrated with the base plate;
   wherein the set of microneedles includes at least a first and a second microneedle,
   wherein the set of microneedles and the base plate comprise a porous ceramic material or a porous ceramic composite material having pores,
   wherein the set of microneedles and the base plate comprise the same porous ceramic material,
   wherein the diameter of the pores ranges from 10 to 200 nanometer,
   wherein the set of microneedles and the base plate are formed together during a single technological step so that the set of microneedles substantially seamlessly transit into the base plate, and
   wherein each microneedle of the set of microneedles comprises a tip that is defined by at least one oblique plane passing through the microneedle,
   wherein the tip of the first microneedle is defined by at least one oblique plane that is different from an oblique plane defining the tip of the second microneedle
   wherein the set of microneedles comprise alumina particles having a grain size of 300-500 nm or zirconia particles having a grain size of 50 nm or less; and
   wherein the alumina particles or the zirconia particles are sintered together to form the porous ceramic material or the porous ceramic composite material having pores.

* * * * *